(12) United States Patent
Grunenfelder et al.

(10) Patent No.: US 7,001,178 B2
(45) Date of Patent: Feb. 21, 2006

(54) METHOD AND APPARATUS FOR USING A DISPLAY ASSOCIATED WITH A DENTAL KILN

(75) Inventors: Robert Grunenfelder, Eschen (LI); Gottfried Rohner, Altstatten (CH)

(73) Assignee: Ivoclar Vivadent A.G., Schaan (LI)

( * ) Notice: Subject to any disclaimer, the term of this patent is extended or adjusted under 35 U.S.C. 154(b) by 0 days.

(21) Appl. No.: 10/971,273

(22) Filed: Oct. 23, 2004

(65) Prior Publication Data

US 2005/0175949 A1 Aug. 11, 2005

(30) Foreign Application Priority Data

Jan. 19, 2004 (DE) .................. 10 2004 002 724

(51) Int. Cl.
 *F27B 21/02* (2006.01)
(52) U.S. Cl. ............ 432/206; 432/51; 433/215; 433/26
(58) Field of Classification Search ........... 432/51, 432/120, 206; 433/26, 215
See application file for complete search history.

(56) References Cited

U.S. PATENT DOCUMENTS

| | | | |
|---|---|---|---|
| 5,653,589 A | | 8/1997 | Kleinmann |
| 5,788,485 A | * | 8/1998 | Grunenfelder et al. ...... 432/250 |
| 5,800,164 A | * | 9/1998 | Pfau ........................... 433/26 |
| 5,997,293 A | * | 12/1999 | Grunenfelder et al. ...... 432/206 |
| 6,132,210 A | | 10/2000 | Lehmann |
| 6,206,691 B1 | | 3/2001 | Lehmann et al. |
| 6,252,202 B1 | * | 6/2001 | Zychek ....................... 219/390 |
| 6,358,047 B1 | | 3/2002 | Lehmann |
| 6,499,998 B1 | | 12/2002 | Kerschbaumer et al. |
| 6,786,726 B1 | | 9/2004 | Lehmann |

FOREIGN PATENT DOCUMENTS

| | | |
|---|---|---|
| DE | 197 54 077 A1 | 6/1999 |
| WO | WO 00/25696 A1 | 5/2000 |

OTHER PUBLICATIONS

CYNOVAD, ShadeScan(™), Mapping the Shades . . . with a single click, Feb. 2002, Montreal, Canada.
Ivoclar Vivadent AG, Programat X1, A high-tech ceramic furnace, prior to Oct. 2004, Schaan, Liechtenstein.
Ivoclar Vivadent AG, Programat P200 furnace, published prior to Oct. 2004, Schaan Liechtenstein.

* cited by examiner

*Primary Examiner*—Gregory Wilson
(74) *Attorney, Agent, or Firm*—John C. Thompson; Alan S. Korman

(57) ABSTRACT

An kiln for dental restoration components is provided, and comprises an indicator having an image screen for displaying information. The image screen is provided with at least two, and in particular at least three, surface areas with which optically distinguishable features, including colors, types and structures, can be represented. The surface areas together essentially form a front and/or side view of at least one tooth.

32 Claims, 4 Drawing Sheets

METHOD AND APPARATUS FOR USING A DISPLAY ASSOCIATED WITH A DENTAL KILN

CROSS-REFERENCE TO RELATED APPLICATIONS

This application claims foreign priority benefits under 35 U.S.C. §119 from German patent application Ser. No. 10 2004 002 724.2 filed Jan. 19, 2004.

TECHNICAL FIELD

The present invention relates to a method and apparatus for using a display associated with a dental kiln, and more particularly to a dental kiln assembly used for firing dental restorations which assembly includes a kiln, a display associated with the kiln, a control circuit associated with the display, an input circuit associated with the control circuit for inputting data corresponding to an image of at least one tooth that is to be restored, or an adjacent tooth, and wherein the control circuit is able to process the data received from the input circuit and to create an image on said display of at least two, and in particular at least three, surface areas with which optically distinguishable features can be represented, the surface areas together essentially forming front and/or side views of a tooth to be restored.

BACKGROUND OF THE INVENTION

A dental kiln or oven having a display is known in the art, for example the Ivoclar Vivadent Programat® X1. With this kiln, various parameters are indicated on a display. This is intended to ensure that the operator of such a kiln selects the correct burning or firing curve. The display may optically compare how the combustion chamber temperature and the temperature of the object that is to be burned or fired differ from one another. Also to be provided is a desired value/actual value comparison.

When a patient visits a dentist for a new crown, the dentist makes an impression from the teeth and defines the colors of the tooth to be restored, or of the adjacent teeth, (e.g. A2, B3, . . . ) with the help of a color key, one such color key being shown in U.S. Pat. No. 5,653,589. Afterwards, the dental technician will receive the impression and a number of a color (e.g. A2) the new crown should have. After he has produced a fitting crown-cap, he has to build up this cap with fluent ceramic material whose material number agrees with the color number he received from the dentist. In a following production step the ceramic material has to be fired in a dental kiln.

If the dental technician works together with a good dentist, he will probably get two colors for the ceramic material, one color defining the incisal area of the tooth and a second color defining the color of the tooth adjacent the gum. What the dental technician doesn't have with this information is the exact run of the border between color one and color two. Therefore there might always be the risk that the new dental restoration doesn't exactly agree with the color of the tooth to be restored, although the technician has used the right ceramic colors.

It has furthermore become known to establish the desired tooth color via specialized computer-enhanced measures, and to transmit appropriate image data to the dental technician. For this purpose, it has been proposed, via a camera, to photograph existing teeth, with the photograph then being used for making available the prescribed tooth colors. One example of such an approach can be found in the shade analyzer shown in U.S. Pat. No. 6,786,726.

With the help of a shade analyzer the dentist makes a photo from the tooth to be restored or one of the neighboring teeth which corresponds at best with the color of the tooth to be restored. Then the photographed tooth will be subdivided in different regions positioned one upon the other beginning from the incisal area to the gum. For each of the different regions an average color and a number of the average color will be determined through a comparison with different colors stored in a control device of the shade analyzer. Then the data will be sent to the dental technician in the form of a picture (e.g., a .jpg file) and information concerning the color numbers of the regions in the form of one or more electronic files.

With such approaches, the tooth colors are established according to perception and visual comparison by the dental technician or the dentist, and appropriate specifications are prescribed for the selection of the tooth colors having the appropriate color codes (also, for example, A2, C1 or the like). The tooth is then divided into appropriate surface areas, and corresponding tooth colors are used during the restoration.

The dental technician then has the pertaining surface areas in front of him or her in a printed form or in some other suitable form during the manufacture of the tooth, and is then expected to prepare the corresponding tooth.

Despite this aid, the results of the restoration are frequently not satisfactory. For example, there can also be misunderstandings or incorrect interpretations with regard to the coding of the pertaining surface areas, especially if the pertaining tooth colors are written down by the dentist in longhand. In addition, a black and white expression makes it very difficult to assess the optical effect of the tooth that is to be restored, so that to this extent one must rely very heavily upon the experience not only of the dentist but also of the dental technician, which of course affects the result of the restoration.

There is also the danger that mistakes or mix-ups can occur, especially if, for example, a number of teeth are to be produced for the same patient, which teeth generally exhibit very little difference in shading.

Whereas fluctuations in color and slight errors can be tolerated in the molar region, the front teeth should have a particularly aesthetic appearance.

OBJECTS AND SUMMARY OF THE INVENTION

It is an object of the present invention to provide a method and apparatus for using a display associated with a dental kiln for the build up of a dental restoration.

More particularly, it is an object of the present invention to provide a dental kiln assembly used for firing dental restorations which assembly includes a kiln, a display associated with the kiln, a control circuit associated with the display, an input circuit associated with the control circuit for inputting data corresponding to an image of at least one tooth that is to be restored, or an adjacent tooth.

It is a further object of the present invention to utilize a novel apparatus including a dental kiln assembly used for firing dental restorations, the assembly including a display or image screen, a control circuit associated with the display, and an input circuit associated with the control circuit; the utilization including the steps of transferring to the input circuit a data set of a tooth to be restored, or of a tooth adjacent the tooth to be restored; and representing on the image screen, surface areas that when viewed together essentially correspond to a front and/or side view of the tooth to be restored, wherein said surface areas are demarcated from one another and each surface area has a distinguishable feature, such as a type, color, brightness or the like, and wherein each feature corresponds to a tooth color of a tooth that is to be produced, and wherein the control circuit is able to process the data received from the input circuit and to create an image on said display of at least two, and in particular at least three, surface areas with which optically distinguishable features can be represented, the surface areas together essentially forming front and/or side views of a tooth to be restored.

The inventive firing kiln is characterized by a special indicator, display or image screen which can display surface areas of a tooth to be restored that, when viewed together, form a front view of a front tooth. An input data port associated with a control circuit may receive data from a dental office which has taken a picture of a tooth to be restored, with the photograph then being used for making available the prescribed tooth colors. Each of the surface areas has a uniform color, a uniform pattern, or the like. Surface areas having the same tooth color have the same optical feature, and to this extent there is effected a well-defined coordination between the desired tooth color and the tooth color that is to be used, but also of their boundary lines, in other words, the determination of where the next tooth color should be used.

The coding is preferably effected pursuant to a known tooth color scheme or coding, and the number of surface areas is also limited, so that, for example, five different colors can be utilized for the front tooth. This does not preclude a greater number of surface areas, for example even twenty surface areas, from being illustrated upon the image screen, so that they offer optically distinguishable information to the dental technician with regard to how the tooth that is to be restored should precisely look.

Making this color information available can, pursuant to the present application, be effected in a particularly expedient manner if it is computer enhanced. For example, the image taken by the dental camera, for example of the neighboring tooth, can be electronically converted into appropriate reference colors by undertaking a color-similarity comparison for each point of color, and representing the corresponding color.

Pursuant to the invention it is expedient if the pertaining data is transmitted, together with the order, to a dental lab, in a suitable manner, such as, for example, per chip card, per e-mail, per diskette, or for example also by a CD that has been burned for this purpose. The direct spatial proximity of the indicator to the kiln ensures that the dental technician, especially during the firing, or the charging of the kiln, has the tooth that is to be restored in his or her field of vision, thereby significantly reducing the probability of mistakes occurring. The correctness of possible handwritten notes does not matter, since the dental camera, based upon appropriate color comparison, reliably delivers the desired colors for the restoration.

Pursuant to a further advantageous embodiment of the present application, the image screen is disposed spatially close to the kiln, and in particular is connected therewith.

Pursuant to a further advantageous embodiment, the kiln is specified for the firing of a tooth that on the image screen is schematically divided into surface areas, or for the firing of a plurality of teeth, of which at least one is illustrated on the image screen such that it is divided into surface areas.

Pursuant to a further advantageous embodiment, the surface areas respectively correspond to different tooth color regions of at least one tooth that is to be fired, further said surface areas are each cohesive and adjacent ones of said surface areas are demarcated from one another in a manner free of transition.

Pursuant to a further advantageous embodiment, surface areas that are present in the same color correspond to the same tooth colors, and said surface areas are additionally provided with a tooth color coding such as "C1", "D2" or another tooth color coding that is illustrated on the image screen within or outside of said surface area.

Pursuant to a further advantageous embodiment, said image screen is connected to a control unit that is provided with a data input by means of which an image and/or a data set having at least the tooth colors of the individual color regions of the image can be fed into or downloaded from said control unit, and a data carrier reader and/or a data input port are provided for a feeding in of the image and the data set.

Pursuant to a further advantageous embodiment, said surface areas are distinguishable from one another by different color surfaces, shadings, brightness, or other patterns, and are illustrated on said image screen with a shape that when viewed together corresponds to the shape of a tooth that is to be produced.

Pursuant to a further advantageous embodiment, said optically distinguishable features include color variations that can be illustrated via specially configured surface areas, and said image screen is connected to a control unit into which can be fed multimedia information that can then be represented in the form of acoustical sequences and/or can be illustrated on said image screen in the form of moved images.

Pursuant to a further advantageous embodiment, information pertaining at least to a tooth that is to be fired is adapted to be fed via a data input into a control unit, and at least a graphic portion of the information is adapted to be illustrated on said image screen with the aid of said control unit.

Pursuant to a further advantageous embodiment, said data input is a modem, a data import/export port of said kiln and/or a data carrier reader that cooperates with said kiln, and said image screen is connected to a control unit, and information is adapted to be fed into said control unit in the form of electronic data.

Pursuant to a further advantageous embodiment, said graphic portion of the information is jpg, bmp, tif, pdf, txt, xls, ppt, avi, etc. data, and a magnitude and/or position of graphic data on said image screen is adapted to be varied with the aid of an input unit that is associated with said image screen.

Pursuant to a further advantageous embodiment, at least those ones of said surface areas that are disposed within an outer contour of the tooth are adapted to be supplied with color information with respect to the tooth colors that are present in these surface areas, and further an input unit is included that is associated with said image screen, with which input unit a cursor can be controlled that is moveable over said surface areas or groups of said surface areas of said image screen, and color information, in particular as a tooth color, respectively indicates only that surface area or group of surface areas on said image screen upon which the cursor is disposed, and the color information of at least one surface area or group of surface areas of said image screen, which color information lies within an outer contour of the tooth, is adapted to be compared with a plurality of tooth colors stored in a control unit of said kiln, with coinciding tooth colors being adapted to be indicated on said image screen, and an existing kiln is adapted to be retrofitted with an indicator having at least two surface areas, especially accompanied by replacement of a control unit of said kiln.

According to a method of operating a kiln for use in the dental field, an indicator is provided in the form of an image screen, and on said image screen, surface areas are represented that when viewed together essentially correspond to a front and/or side view of at least one tooth, said surface areas are demarcated from one another and each surface area has a distinguishable feature, such as a type, color brightness or the like, and each feature corresponds to a tooth color of a tooth that is to be produced.

Pursuant to a further advantageous embodiment, for producing a data set for tooth color reproduction, the tooth is divided into surface areas having similar tooth colors, wherein the surface areas adjoin one another, and in addition to tooth color regions prescribed in broad illustration, patient-specific data is stored in said data set, and an image illustrating at least one tooth, and/or data from a dentist or dental technician, are transmitted to a dental lab by appropriately setting up said kiln.

Pursuant to a further advantageous embodiment, an image and/or data set is adapted to be fed into a control unit of said kiln via a data port and/or a data carrier reader, and via said surface areas in coded form, i.e. by colors, shading or the like, optically distinguishable features of a tooth adjacent to the tooth that is to be restored can be illustrated, and an input unit is provided that is associated with said image screen and that controls a cursor, wherein tooth colors of the optically distinguishable features are indicated when the cursor is disposed in one of said surface areas.

Pursuant to a further advantageous embodiment, tooth colors of each of said surface areas in which said cursor is found are indicated, and a control unit is provided that has a comparator, and in said control unit a plurality of tooth colors are stored and a pertaining tooth color is indicated when a cursor on said image screen is disposed in a surface area that indicates the pertaining tooth color, and a plurality of surface areas can be grouped together via the cursor, an average color of all of said surface areas is determined and is compared with the stored tooth colors and a pertaining tooth color is indicated.

Pursuant to a further advantageous embodiment, said input unit contains a zoom and/or movement device with which the position of the image screen, as well as the size of the image illustrated on the image screen, can be varied, and a type of frame can be achieved with said input unit about a plurality of image points or groups of image points, average colors are determined within said frame and are compared with stored tooth colors, and coinciding tooth colors are indicated on said image screen.

Further specific features of the present invention will be described in detail subsequently.

The above objects, and other objects and advantages of the present invention, will appear more clearly from the following specification in conjunction with the accompanying schematic drawings.

DESCRIPTION OF SPECIFIC EMBODIMENTS

Figure 1:
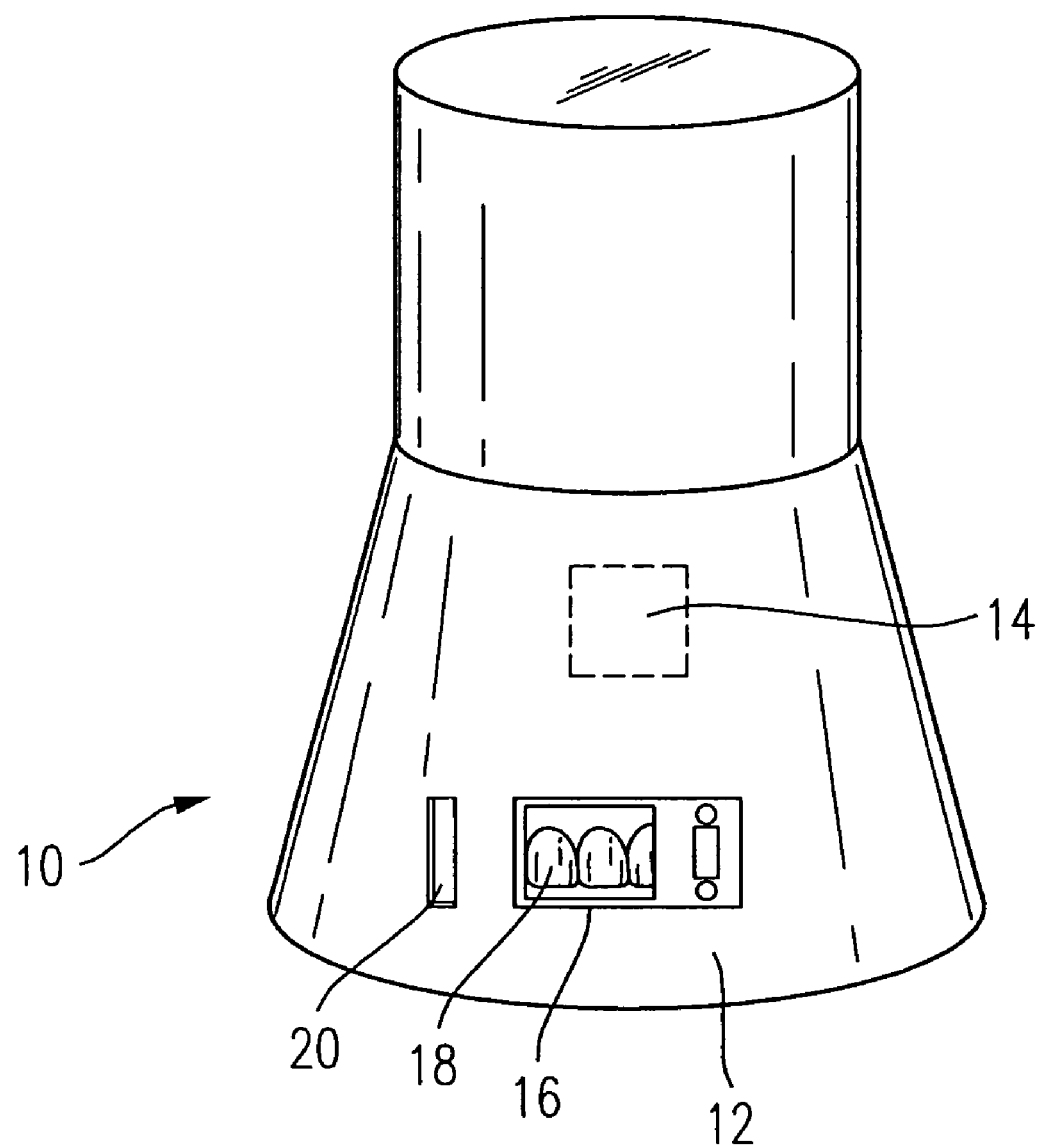
FIG. 1 is a perspective view of a first exemplary embodiment of an inventive kiln.

Referring now to the drawings in detail, the firing kiln or kiln 10 illustrated in FIG. 1 is provided with control elements 12 that act upon a schematically indicated control device 14. The control device serves, among other things, for the control of the firing curve pursuant to the set firing curves. The control device also makes available the information that can be visibly indicated for the dental technician on an inventive indicator 16. The indicator 16 shows the contours of a front tooth 18 and surface areas that pursuant to the invention are to be developed in a particular manner. The surface areas themselves are illustrated in FIGS. 2 and 3.

The kiln 10 is furthermore provided with a suitable input device. In the illustrated embodiment, the reading or input slot 20 of a chip card is illustrated, which is made available to the dental technician together with the order for the firing of the desired restoration.

It is to be understood that other types of data transmission are also possible.

Figure 2:
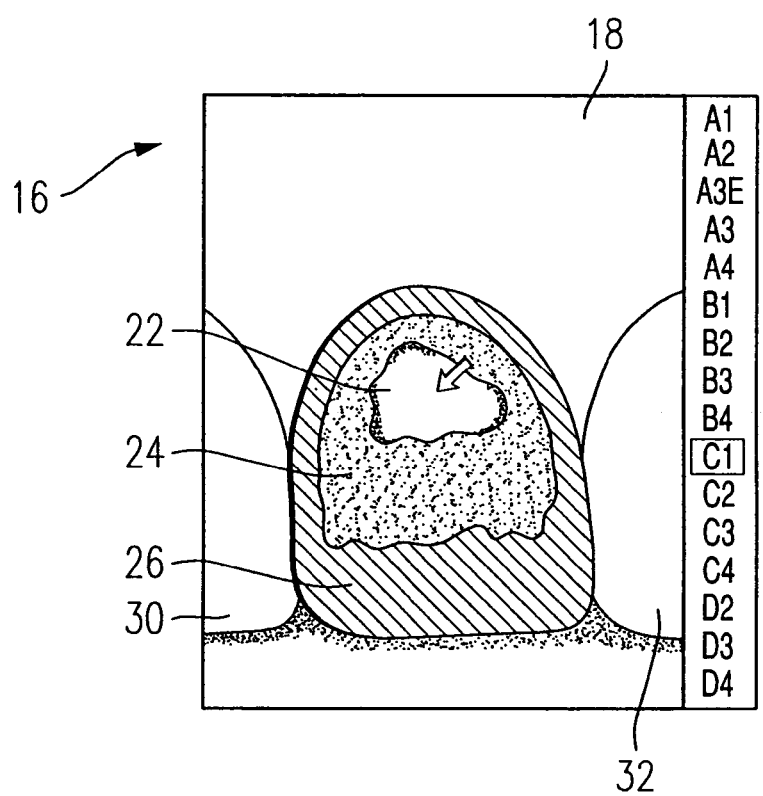
FIG. 2 is a detailed view of an inventive kiln, namely of the indicator.
Figure 3:
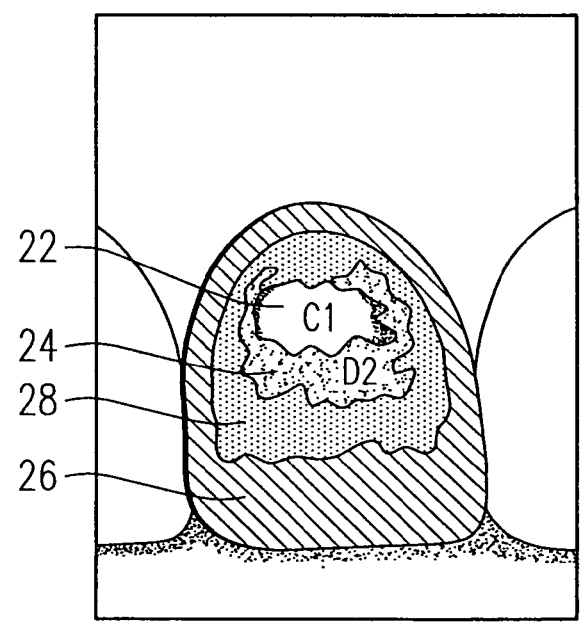
FIG. 3 is a view of the indicator of FIG. 2, however showing different surface areas.

In FIG. 2, the front tooth 18 is illustrated in detail on the indicator 16. In the illustrated embodiment, the front tooth has three surface areas 22, 24 and 26, which are each essentially cohesive and show different colors of the tooth. For this purpose, the surface area 22 is coded with the indication "C1", which corresponds to a color or shade of a known color code. Prescribed for the surface area 24 is the shade D2, and for the surface area 26 the shade E1.

The color or shade reproduction is effected on the indicator by appropriate gradations of brightness or shadings. Pursuant to a modified embodiment, different colors are provided for each surface area, in which connection it is to be understood that these colors do not correspond to the actual tooth colors, but rather enable the clear differentiation.

A complex arrangement or configuration of tooth surface areas can be seen in FIG. 3. Here, in addition to the three surface areas 22, 24 and 26, a fourth surface area 28 is provided, whereby each surface area has an asymmetrical shape that approximates the natural color variation, and only partially cohesive surface areas are present. So-called color islands are characterized as being grouped together by suitable optical features such as shading or the like.

The tooth that is to be restored is completely visible on the indicator 16 in a side view, in other words from the front. The respectively adjacent mesial and distal front teeth 30 and 32 are each cut off but slightly visible, whereby at this location no surface areas are illustrated.

An appropriate image can be electronically made directly available based upon the image taken by a dental camera after appropriate image processing for making available the desired tooth that is to be restored; this is done by providing threshold values for each shade that provide corresponding surfaces.

It is to be understood that together with the transmission of shades to the inventive indicator via the appropriate chip card, the pertaining patient data, including the precise identification of the tooth that is to be restored, can also be transmitted.

Pursuant to a particularly expedient embodiment of the invention, the control device 14 is equipped with a comparator, which then can also be fed the raw data of the dental camera, after appropriate processing, for the establishment of the image data of the tooth that is to be restored. Based upon reference tables of the existing tooth colors, the comparator then produces the inventive surface areas, which pursuant to the invention can then be illustrated upon the indicator 16.

Figure 4:
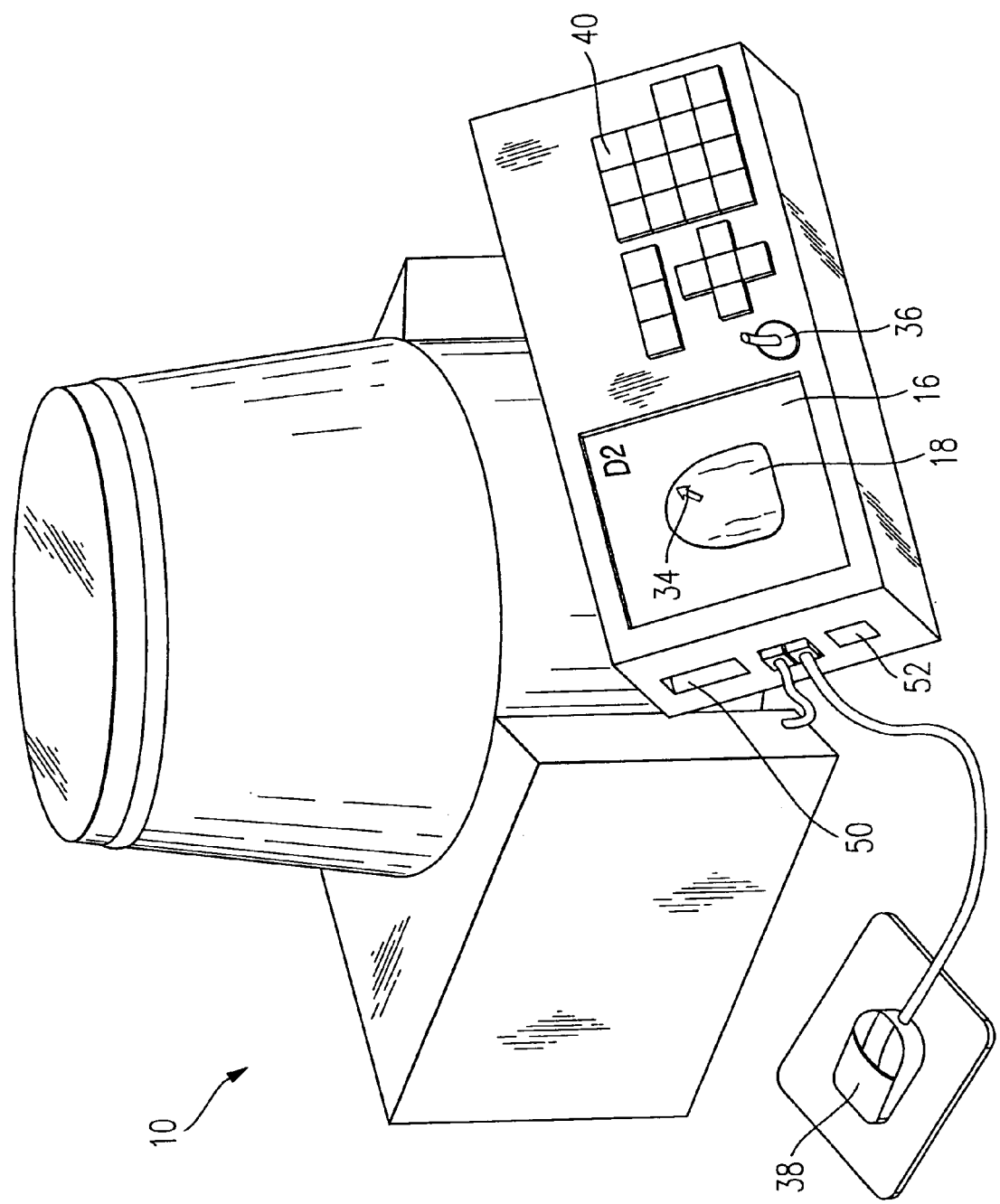
FIG. 4 is a view of a further exemplary embodiment of an inventive kiln.

The firing oven or kiln 10 illustrated in FIG. 4 is provided with an image screen as the indicator 16, which in contrast to the embodiment of FIG. 1 is arranged separately, yet is adjacent to the kiln. Here also one can see an image of a front tooth 18, which again is divided into surface areas, although this is not shown in FIG. 4.

With this embodiment, there is also disposed on the image screen a pointer or a cursor 34, which can be controlled via a type of joy stick 36 or a mouse 38. When a specific surface area is selected by the control with the joy stick 36 or the mouse 38, the pertaining tooth color is indicated, for example "D2", as illustrated on the image screen 16.

By means of a keyboard, specific surfaces can be selected, with the control being provided such that one keeps a key pressed down, and then via the cursor generates a frame on the image screen.

The inventive kiln is furthermore provided with a data carrier reader 50 and a data input 52, by means of which suitable data can be conveyed to the kiln for the transmission of the desired information.

It is also possible to embody the port 52 in a bidirectional manner in order, for example, to confirm the successful transmission of data.

Pursuant to a further modified embodiment, a color analysis is also performed on the image screen of the kiln by color comparison. For this purpose, a photo produced by a digital camera is preferably read in digital form via the data input 52. The color analysis is then effected by comparison with the tooth colors stored in the kiln.

Figure 5:
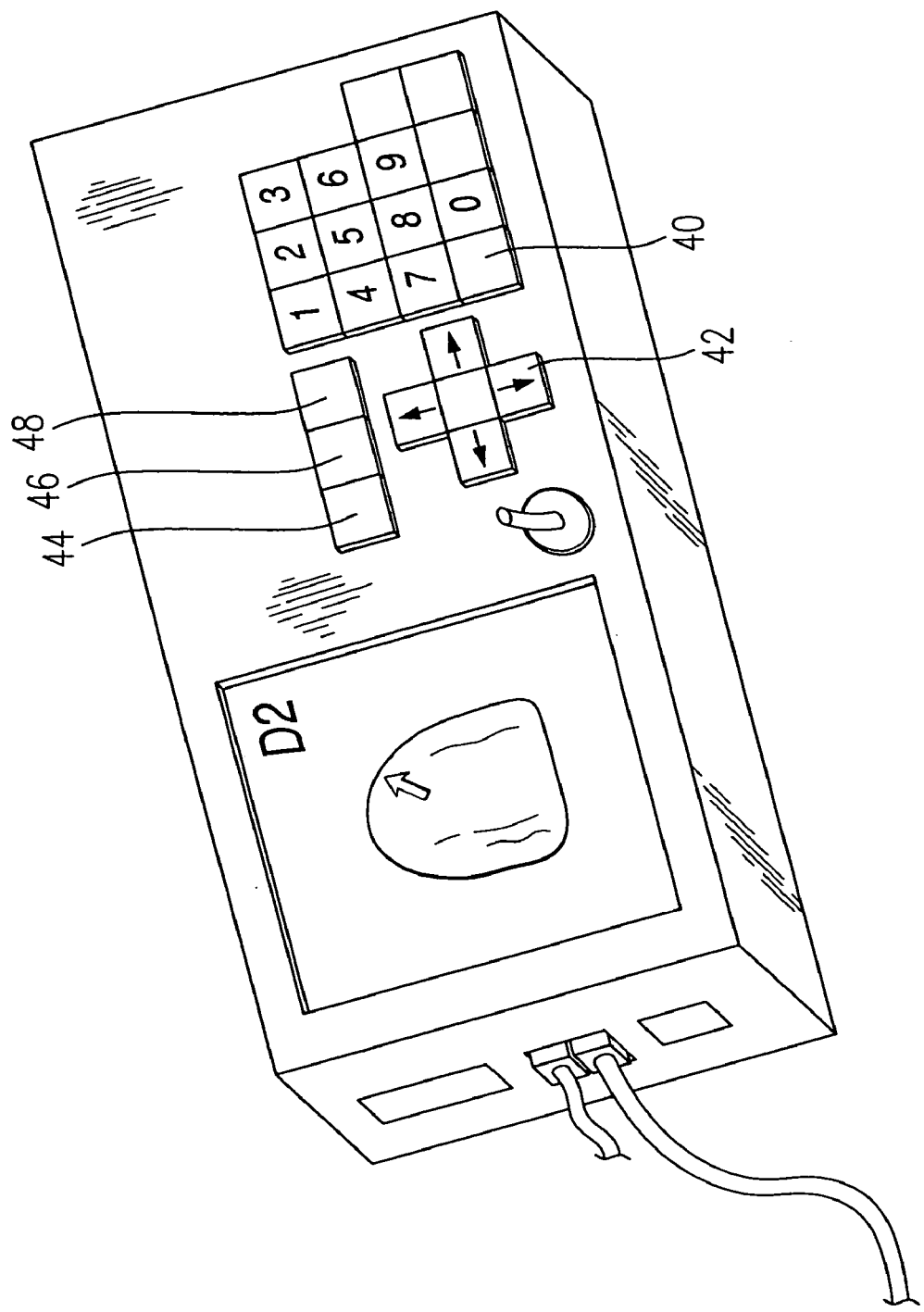
FIG. 5 is an enlarged view of a portion of the kiln of the embodiment of FIG. 4.

FIG. 5 shows a somewhat enlarged view of the unit comprising the image screen, keyboard and pointer. The keyboard 40 is also provided with cursor keys 42 for a selective operation, as well as respective keys for "enlargement" 44, "reduction" 46, and for "shift image screen detail" 48. With such keys, it is also possible to establish a color as desired, or for a type of processing to be undertaken.

If necessary, the inventive image screen can also be retrofitted, whereby it is expedient to exchange the control unit of the kiln for a control unit that is suitable for the control of the image screen.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A method of using a display associated with a dental kiln used for firing dental restorations, there being a control circuit associated with the display and an input circuit associated with the control circuit; the method including the steps of:
   transferring via the input circuit to the control circuit a data set of a tooth to be restored, or of a tooth adjacent the tooth to be restored; and
   using the control circuit to represent on the image screen, surface areas that when viewed together essentially correspond to a front and/or side view of the tooth to be restored, wherein the surface areas are demarcated from one another and each surface area has a distinguishable feature, such as a type, color, brightness or the like, and wherein each feature corresponds to a tooth color of a tooth that is to be produced.

2. A method according to claim 1, wherein for producing a data set for tooth color reproduction, the tooth is divided into surface areas having similar tooth colors, wherein the surface areas adjoin one another.

3. A method according to claim 2, wherein in addition to tooth color regions prescribed in broad illustration, patient-specific data is stored in the data set.

4. A method according to claim 2, wherein the image data set is adapted to be fed into the control circuit of the kiln via a data port and/or a data carrier reader.

5. A method according to claim 2, wherein optically distinguishable features of a tooth adjacent to the tooth that is to be restored can be illustrated via surface areas in coded form, i.e. by colors, shading or the like.

6. A method according to claim 1, wherein an input unit in the form of a mouse or the like is associated with the display for controlling a cursor on the display, and wherein the method further includes the step of using the input unit to control the cursor on the display, and wherein tooth colors of the optically distinguishable features are indicated when the cursor is disposed in one of the surface areas.

7. A method according to claim 6, wherein tooth colors of each of the surface areas in which the cursor is found are indicated.

8. A method according to claim 6, wherein the input unit contains a zoom and/or movement device with which the position of the image on the image screen, as well as the size of the image illustrated on the image screen, can be varied.

9. A method according to claim 6, wherein a type of frame can be achieved with the input unit about a plurality of image points or groups of image points, wherein average colors are determined within the frame and are compared with stored tooth colors, and wherein coinciding tooth colors are indicated on the image screen.

10. A method according to claim 1, wherein the control unit has a comparator, and wherein in the control unit a plurality of tooth colors are stored, and wherein a pertaining tooth color is indicated when a cursor on the image screen is disposed in a surface area that indicates the pertaining tooth color.

11. A method according to claim 10, wherein a plurality of surface areas can be grouped together via the cursor, wherein an average color of all of the surface areas is determined and is compared with the stored tooth colors and a pertaining tooth color is indicated.

12. A dental kiln assembly used for firing dental restorations; the assembly comprising:
   a kiln;
   a display associated with the kiln;
   a control circuit associated with the display; and
   an input circuit associated with the control circuit, said input circuit inputting data corresponding to an image of at least one tooth that is to be restored, or an adjacent tooth, to the control circuit:

characterized by:

the control circuit being able to process the data received from the input circuit and to create an image on the display of at least two, and in particular at least three, surface areas with which optically distinguishable features can be represented, and wherein the surface areas together essentially form a front and/or side view of a tooth to be restored.

13. The dental kiln assembly according to claim 12, wherein the control surface causes surface areas of the image that is present to be in the same colors of the corresponding tooth to be restored.

14. The dental kiln assembly according to claim 12, wherein a data set having at least the tooth colors of the individual color regions of the image can be fed into or downloaded.

15. The dental kiln assembly according to claim 14, wherein the input circuit includes a data carrier reader and/or a data input port for feeding in of the image and the data set.

16. The dental kiln assembly according to claim 12, wherein the display is connected to the control unit into which can be fed multimedia information that can then be represented in the form of acoustical sequences and/or can be illustrated on the display in the form of moved images.

17. The dental kiln assembly according to claim 12, wherein the input circuit includes a modem, a data import/export port of the kiln, and/or a data carrier reader that cooperates with the kiln.

18. The dental kiln assembly according to claim 12, wherein at the surface areas are disposed within an outer contour of the tooth, and are adapted to be supplied with color information with respect to the tooth colors that are present in these surface areas.

19. The dental kiln assembly according to claim 18, which further includes an input unit that is associated with the display, the input unit being in the form of a mouse or the like for controlling a cursor on the display, and with which a cursor can be controlled that is moveable over the surface areas or groups of the surface areas of the image screen, and wherein color information, in particular as a tooth color, respectively indicates only that surface area or group of surface areas on the image screen upon which the cursor is disposed.

20. The dental kiln assembly according to claim 19, wherein the color information of at least one surface area or group of surface areas of said image screen, which color information lies within an outer contour of the tooth, is adapted to be compared with a plurality of tooth colors stored in a control unit of said kiln, with coinciding tooth colors being adapted to be indicated on said image screen.

21. The dental kiln assembly according to claim 12, wherein said surface areas are each cohesive.

22. The dental kiln assembly according to claim 12, wherein adjacent ones of said surface areas are demarcated from one another in a manner free of transition.

23. The dental kiln assembly according to claim 12, wherein surface areas that are present in the same color correspond to the same tooth colors.

24. The dental kiln assembly according to claim 12, wherein said surface areas are additionally provided with a tooth color coding that is illustrated on said image screen within or outside of said surface area.

25. The dental kiln assembly according to claim 12, wherein said surface areas are distinguishable from one another by different color surfaces, shadings, brightness, or other patterns.

26. The dental kiln assembly according to claim 12, wherein said surface areas are illustrated on said image screen with a shape that when viewed together corresponds to the shape of a tooth that is to be produced.

27. The dental kiln assembly according to claim 12, wherein said optically distinguishable features include color variations that can be illustrated via specially configured surface areas.

28. The dental kiln assembly according to claim 12, wherein information pertaining at least to a tooth that is to be burned is adapted to be fed via a data input into a control unit, and at least a graphic portion of the information is adapted to be illustrated on said image screen with the aid of said control unit.

29. The dental kiln assembly according to claim 12, wherein said image screen is connected to a control unit, and wherein information is adapted to be fed into said control unit in the form of electronic data.

30. The dental kiln assembly according to claim 29, wherein said graphic portion of the information is jpg, bmp, tif, pdf, txt, xls, ppt, avi, etc. data.

31. The dental kiln assembly according to claim 12, wherein a magnitude and/or position of graphic data on said image screen is adapted to be varied with the aid of an input unit that is associated with said image screen.

32. The dental kiln assembly according to claim 12, wherein an existing kiln is adapted to be retrofitted with an indicator having at least two surface areas, especially accompanied by replacement of a control unit of said kiln.

* * * * *